(12) United States Patent
Tehrani et al.

(10) Patent No.: US 8,265,759 B2
(45) Date of Patent: Sep. 11, 2012

(54) DEVICE AND METHOD FOR TREATING DISORDERS OF THE CARDIOVASCULAR SYSTEM OR HEART

(75) Inventors: Amir J. Tehrani, Los Altos, CA (US); Rose Province, San Jose, CA (US)

(73) Assignee: RMX, LLC, San Francisco, CA (US)

( * ) Notice: Subject to any disclaimer, the term of this patent is extended or adjusted under 35 U.S.C. 154(b) by 822 days.

(21) Appl. No.: 12/082,057

(22) Filed: Apr. 8, 2008

(65) Prior Publication Data

US 2008/0188904 A1 Aug. 7, 2008

Related U.S. Application Data

(63) Continuation-in-part of application No. 12/069,823, filed on Feb. 13, 2008, now abandoned, which is a continuation-in-part of application No. 12/004,932, filed on Dec. 21, 2007, now abandoned, which is a continuation-in-part of application No. 11/981,342, filed on Oct. 31, 2007, now Pat. No. 8,140,164, which is a continuation-in-part of application No. 11/480,074, filed on Jun. 29, 2006, now Pat. No. 8,160,711, which is a continuation-in-part of application No. 11/271,726, filed on Nov. 10, 2005, now Pat. No. 7,970,475, which is a continuation-in-part of application No. 10/966,484, filed on Oct. 15, 2004, now abandoned, and a continuation-in-part of application No. 10/966,474, filed on Oct. 15, 2004, and a continuation-in-part of application No. 10/966,472, filed on Oct. 15, 2004, now Pat. No. 8,200,336, and a continuation-in-part of application No. 10/966,421, filed on Oct. 15, 2004, which is a continuation-in-part of application No. 10/686,891, filed on Oct. 15, 2003.

(60) Provisional application No. 60/925,024, filed on Apr. 18, 2007.

(51) Int. Cl.
*A61N 1/18* (2006.01)
(52) U.S. Cl. .............................. 607/42; 607/20
(58) Field of Classification Search ............ 607/42, 607/20
See application file for complete search history.

(56) References Cited

U.S. PATENT DOCUMENTS

| | | |
|---|---|---|
| 3,773,051 A | 11/1973 | Holcomb et al. |
| 4,827,935 A | 5/1989 | Geddes et al. |
| 4,830,008 A | 5/1989 | Meer |
| 5,056,519 A | 10/1991 | Vince |

(Continued)

FOREIGN PATENT DOCUMENTS

DE  112004001957 T5  8/2006

(Continued)

OTHER PUBLICATIONS

Abraham, W., "Advances in Heart Failure Therapy in the Primary Care Context," *Medscape Family Medicine/Primary Care*, 7 pages, 2004.

(Continued)

*Primary Examiner* — Niketa Patel
*Assistant Examiner* — Alyssa M Alter
(74) *Attorney, Agent, or Firm* — Levine Bagade Han LLP

(57) ABSTRACT

A device and method are provided to treat heart failure by stimulating to cause diaphragm contraction.

25 Claims, 5 Drawing Sheets

U.S. PATENT DOCUMENTS

| | | | |
|---|---|---|---|
| 5,146,918 A | 9/1992 | Kallok et al. | |
| 5,174,287 A | 12/1992 | Kallok et al. | |
| 5,190,036 A | 3/1993 | Linder | |
| 5,211,173 A | 5/1993 | Kallok et al. | |
| 5,215,082 A | 6/1993 | Kallok et al. | |
| 5,233,983 A | 8/1993 | Markowitz | |
| 5,265,604 A | 11/1993 | Vince | |
| 5,281,219 A | 1/1994 | Kallok | |
| 5,300,094 A | 4/1994 | Kallok et al. | |
| 5,423,327 A | 6/1995 | Clauson et al. | |
| 5,483,969 A | 1/1996 | Testerman et al. | |
| 5,485,851 A | 1/1996 | Erickson | |
| 5,522,862 A | 6/1996 | Testerman et al. | |
| 5,524,632 A | 6/1996 | Stein et al. | |
| 5,540,731 A | 7/1996 | Testerman | |
| 5,540,732 A | 7/1996 | Testerman | |
| 5,540,733 A | 7/1996 | Testerman et al. | |
| 5,546,952 A | 8/1996 | Erickson | |
| 5,549,655 A | 8/1996 | Erickson | |
| 5,572,543 A | 11/1996 | Heinemann et al. | |
| 5,678,535 A | 10/1997 | DiMarco | |
| 5,766,228 A | 6/1998 | Bonnet et al. | |
| 5,797,923 A | 8/1998 | Aiyar et al. | |
| 5,800,470 A | 9/1998 | Stein et al. | |
| 5,814,086 A | 9/1998 | Hirschberg et al. | |
| 5,830,008 A | 11/1998 | Broschard, III | |
| 5,876,353 A | 3/1999 | Riff | |
| 5,895,360 A | 4/1999 | Christopherson et al. | |
| 5,911,218 A | 6/1999 | DiMarco | |
| 5,944,680 A | 8/1999 | Christopherson et al. | |
| 6,021,352 A | 2/2000 | Christopherson et al. | |
| 6,099,479 A | 8/2000 | Christopherson et al. | |
| 6,212,435 B1 | 4/2001 | Lattner et al. | |
| 6,224,562 B1 | 5/2001 | Lurie et al. | |
| 6,251,126 B1 | 6/2001 | Ottenhoff et al. | |
| 6,269,269 B1 | 7/2001 | Ottenhoff et al. | |
| 6,312,399 B1 | 11/2001 | Lurie et al. | |
| 6,314,324 B1 | 11/2001 | Lattner et al. | |
| 6,345,202 B2 | 2/2002 | Richmond et al. | |
| 6,415,183 B1 | 7/2002 | Scheiner et al. | |
| 6,463,327 B1 | 10/2002 | Lurie et al. | |
| 6,480,733 B1 | 11/2002 | Turcott | |
| 6,489,447 B1 | 12/2002 | Basey et al. | |
| 6,512,949 B1 | 1/2003 | Combs et al. | |
| 6,527,729 B1 | 3/2003 | Turcott | |
| 6,542,774 B2 | 4/2003 | Hill et al. | |
| 6,572,543 B1 | 6/2003 | Christopherson et al. | |
| 6,574,507 B1 | 6/2003 | Bonnet | |
| 6,587,725 B1 | 7/2003 | Durand et al. | |
| 6,587,726 B2 | 7/2003 | Lurie et al. | |
| 6,589,188 B1 | 7/2003 | Street et al. | |
| 6,600,949 B1 | 7/2003 | Turcott | |
| 6,633,779 B1 | 10/2003 | Schuler et al. | |
| 6,651,652 B1 | 11/2003 | Wang | |
| 6,731,984 B2 | 5/2004 | Cho et al. | |
| 6,735,479 B2 | 5/2004 | Fabian et al. | |
| 6,752,765 B1 | 6/2004 | Jensen et al. | |
| 6,770,022 B2 | 8/2004 | Mechlenburg et al. | |
| 6,811,537 B2 | 11/2004 | Bardy | |
| 6,830,548 B2 | 12/2004 | Bonnet et al. | |
| 6,881,192 B1 | 4/2005 | Park | |
| 6,908,437 B2 | 6/2005 | Bardy | |
| 7,058,453 B2 | 6/2006 | Nelson et al. | |
| 7,070,568 B1 | 7/2006 | Koh et al. | |
| 7,082,331 B1 | 7/2006 | Park et al. | |
| 7,117,032 B2 | 10/2006 | Childre et al. | |
| 7,277,757 B2 | 10/2007 | Casavant et al. | |
| 7,532,934 B2 | 5/2009 | Lee et al. | |
| 7,610,094 B2 | 10/2009 | Stahmann et al. | |
| 7,840,270 B2 | 11/2010 | Ignagni et al. | |
| 7,970,475 B2 | 6/2011 | Tehrani et al. | |
| 7,979,128 B2 | 7/2011 | Tehrani et al. | |
| 8,116,872 B2 | 2/2012 | Tehrani et al. | |
| 2002/0049482 A1 | 4/2002 | Fabian et al. | |
| 2002/0193697 A1 | 12/2002 | Cho et al. | |
| 2002/0193839 A1 | 12/2002 | Cho et al. | |
| 2003/0127091 A1 | 7/2003 | Chang | |
| 2003/0153953 A1 | 8/2003 | Park et al. | |
| 2003/0153954 A1 | 8/2003 | Park et al. | |
| 2003/0153955 A1 | 8/2003 | Park et al. | |
| 2003/0153956 A1 | 8/2003 | Park et al. | |
| 2003/0195571 A1 | 10/2003 | Burnes et al. | |
| 2003/0204213 A1 | 10/2003 | Jensen et al. | |
| 2003/0225339 A1 | 12/2003 | Orr et al. | |
| 2004/0044377 A1 | 3/2004 | Larsson | |
| 2004/0059240 A1 | 3/2004 | Cho et al. | |
| 2004/0077953 A1 | 4/2004 | Turcott | |
| 2004/0088015 A1 | 5/2004 | Casavant et al. | |
| 2004/0111040 A1 | 6/2004 | Ni et al. | |
| 2004/0116784 A1* | 6/2004 | Gavish | 600/300 |
| 2004/0122484 A1 | 6/2004 | Hatlestad et al. | |
| 2004/0134496 A1 | 7/2004 | Cho et al. | |
| 2004/0138719 A1 | 7/2004 | Cho et al. | |
| 2004/0176809 A1 | 9/2004 | Cho et al. | |
| 2004/0199221 A1 | 10/2004 | Fabian et al. | |
| 2004/0225226 A1 | 11/2004 | Lehrman et al. | |
| 2004/0237963 A1 | 12/2004 | Berthon-Jones | |
| 2005/0021102 A1 | 1/2005 | Ignagni et al. | |
| 2005/0039745 A1 | 2/2005 | Stahmann et al. | |
| 2005/0043644 A1 | 2/2005 | Stahmann et al. | |
| 2005/0043772 A1 | 2/2005 | Stahmann et al. | |
| 2005/0055060 A1 | 3/2005 | Koh et al. | |
| 2005/0061315 A1 | 3/2005 | Lee et al. | |
| 2005/0061319 A1 | 3/2005 | Hartley et al. | |
| 2005/0061320 A1 | 3/2005 | Lee et al. | |
| 2005/0065563 A1 | 3/2005 | Scheiner | |
| 2005/0065567 A1 | 3/2005 | Lee et al. | |
| 2005/0074741 A1 | 4/2005 | Lee et al. | |
| 2005/0076909 A1 | 4/2005 | Stahmann et al. | |
| 2005/0080461 A1 | 4/2005 | Stahmann et al. | |
| 2005/0085734 A1 | 4/2005 | Tehrani | |
| 2005/0085865 A1 | 4/2005 | Tehrani | |
| 2005/0085866 A1 | 4/2005 | Tehrani | |
| 2005/0085867 A1 | 4/2005 | Tehrani et al. | |
| 2005/0085868 A1 | 4/2005 | Tehrani et al. | |
| 2005/0085869 A1 | 4/2005 | Tehrani et al. | |
| 2005/0101833 A1 | 5/2005 | Hsu et al. | |
| 2005/0107860 A1 | 5/2005 | Ignagni et al. | |
| 2005/0115561 A1 | 6/2005 | Stahmann et al. | |
| 2005/0119711 A1 | 6/2005 | Cho et al. | |
| 2005/0145246 A1 | 7/2005 | Hartley et al. | |
| 2005/0148897 A1 | 7/2005 | Cho et al. | |
| 2005/0165457 A1 | 7/2005 | Benser et al. | |
| 2005/0224076 A1 | 10/2005 | Pflichner et al. | |
| 2005/0240240 A1 | 10/2005 | Park et al. | |
| 2005/0261600 A1 | 11/2005 | Aylsworth | |
| 2005/0261747 A1 | 11/2005 | Schuler et al. | |
| 2006/0030894 A1 | 2/2006 | Tehrani | |
| 2006/0036294 A1 | 2/2006 | Tehrani | |
| 2006/0058852 A1 | 3/2006 | Koh et al. | |
| 2006/0064030 A1 | 3/2006 | Cosentino et al. | |
| 2006/0064325 A1 | 3/2006 | Matsumoto et al. | |
| 2006/0122622 A1 | 6/2006 | Truckai et al. | |
| 2006/0122661 A1 | 6/2006 | Mandell | |
| 2006/0122662 A1 | 6/2006 | Tehrani | |
| 2006/0142815 A1 | 6/2006 | Tehrani et al. | |
| 2006/0149334 A1 | 7/2006 | Tehrani et al. | |
| 2006/0155341 A1 | 7/2006 | Tehrani et al. | |
| 2006/0167523 A1 | 7/2006 | Tehrani et al. | |
| 2006/0224211 A1 | 10/2006 | Durand et al. | |
| 2006/0247729 A1 | 11/2006 | Tehrani et al. | |
| 2006/0282131 A1 | 12/2006 | Caparso et al. | |
| 2007/0021795 A1 | 1/2007 | Tehrani | |
| 2007/0156199 A1 | 7/2007 | Koh et al. | |
| 2008/0021506 A1 | 1/2008 | Grocela | |
| 2008/0167695 A1 | 7/2008 | Tehrani et al. | |
| 2008/0177347 A1 | 7/2008 | Tehrani et al. | |
| 2008/0183239 A1 | 7/2008 | Tehrani et al. | |
| 2008/0183240 A1 | 7/2008 | Tehrani et al. | |
| 2008/0188903 A1 | 8/2008 | Tehrani et al. | |
| 2008/0208281 A1 | 8/2008 | Tehrani et al. | |
| 2011/0230932 A1 | 9/2011 | Tehrani et al. | |

FOREIGN PATENT DOCUMENTS

| | | |
|---|---|---|
| DE | 112004001953 T5 | 10/2006 |
| DE | 112004001954 T5 | 10/2006 |
| WO | WO 86/00234 | 1/1986 |

| WO | WO 2005/037077 | 4/2005 |
| WO | WO 2005/037172 | 4/2005 |
| WO | WO 2005/037173 | 4/2005 |
| WO | WO 2005/037174 | 4/2005 |
| WO | WO 2005/037220 | 4/2005 |
| WO | WO 2005/037366 | 4/2005 |
| WO | WO 2007/058938 | 5/2007 |

OTHER PUBLICATIONS

Aiyar, H. et al, "Laparoscopic Implant Device for Intermuscular Electrodes," *IEEE-EMBC and CMBCC*, pp. 1167-1168, 1995.

Aiyar, H. et al, "Laparoscopic Implant Instrument for the Placement of Intramuscular Electrodes in the Diaphragm," *Transactions on Rehabilitation Engineering*, pp. 360-371, Sep. 1999.

Arzt, M. et al, "Treatment of Sleep Apnea in Heart Failure," *AJRCCM*, 36 pages, Mar. 9, 2006.

Bernardi, L. et al, "Effect of Rosary Prayer and Yoga Mantras on Autonomic Cardiovascular Rhythms: Comparative Study," *BMJ*, 323:22-29, Dec. 2001.

Bernardi, L. et al, "Slow Breathing Increases Arterial Baroreflex sensitivity in Patients with Chronic Heart Failure," *Circulation*, 105;143-145, 2002, *American Heart Association*.

Bradley, T.D. et al, "Sleep Apnea and Heart Failure, Part I: Obstructive Sleep Apnea," *Circulation*, pp. 1671-1678, Apr. 1, 2003.

Boston Scientific, "Diaphragm Stimulation During Daily LV Lead impedance Measurements", Product Education Brochure, 2 pages, Sep. 26, 2008.

DiMarco, A F., "Combined Intercostal and Diaphragm Pacing to Provide Artificial Ventilation in Patients With Tetraplegia" *Arch Phys Med Rehabil*, vol. (86), pp. 1200-1207, 2005.

DiMarco, A.F. et al, "Phrenic Nerve Pacing in a Tetraplegic Patient via Intramuscular Diaphragm Electrodes," *American Journal of Respiratory and Critical Care Medicine*, 144:1604-1606, 2002.

Fessler, H.E, "Heart-Lung Interactions: Applications in the Critically Ill," *Eur. Respir. J.*, vol. 10, pp. 226-237, 1997.

Fichter, J. et al, "Sleep-Related Breathing Disorders are Associate with Ventricular Arrhythmias in Patients with an Implantable Cardioverter-Defibrillator," *Chest*, vol. 122, pp. 558-561, Aug. 2002.

Garrigue, S. et al "Sleep Apnea: A New Indication for Cardiac Pacing?," *Pace*, vol. 27, pp. 204-211, Feb. 2004.

Glenn, W. W. L., "Diaphragm Pacing: Present Status," *PACE*, 1:357-370, Jul.-Sep. 1978.

Glenn, W., et al. "Diaphragm Pacing" *Journal of Thoracic and Cardiovascular Surgery*, vol. (75):2, pp. 273-281, 1978.

Gosselink, R. "Controlled Breathing and Dyspnea in Patients With Chronic Obstructive Pulmonary Disease," *Journal of Rehabilitaiton Research and Development*, 40(5):20-31, Supplement 2, Sep./Oct. 2003.

Harish, A. et al, "Laparoscopic Implant Device for Intramuscular Electrodes," *IEEE-EMBC and CMBCC*, pp. 1167-1168, 1995.

Hayano, J. et al "Respiratory Sinus Arrhythmia: A Phenomenon Improving Pulmonary Gas Exchange and Circulatory Efficiency," *Circulation*, vol. 94, pp. 842-847, 1996.

Heinzer, R. et al, "Lung Volume and Continuous Positive Airway Pressure Requirements in Obstructive Sleep Apeau" *American Journal of Respiratory and Critical Care Medicine*, vol. 172, pp. 114-117, 2005.

Hennersdorf, M.G. et al, "Chemoreflexsensitivity in Chronic Heart Failure Patients," *European Journal of Heart Failure*, vol. 3, pp. 679-684, 2001.

Iazzo, P. ed., "Handbook of Cardiac Anatomy, Physiology, and Devices", p. 398, 2009.

Ishii, K. et al "Effects of Bilateral Transvenous Diaphragm Pacing on Hemodynamic Function in Patients after Cardiac Operations," *J Thorac Cardiovasc Surg*, vol. 100, pp. 108-114, 1990.

Javaheri, S. et al, "Sleep Apnea in 81 Ambulatory Male Patients with Stable Heart Failure: Types and Their Prevalences, Consequences, and Presentations," *Circulation*, vol. 97, pp. 2154-2159, 1998.

Jensen, A. et al, "Signal Transduction in Smooth Muscle: Airway caliber in healthy and asthmatic subjects effects of bronchial challenge and deep inspirations," *J. Appl Physiol*, 91:506-515, 2001.

Kohnlein, T. et al, "Central Sleep Apnea Syndrome in Patients with Chronic Heart Disease: a Critical Review of the Current Literature," *Thorax*, vol. 57, pp. 547-554, 2002.

Krachman, S. et al "Comparison of Oxygen Therapy with Nasal Continuous Positive Airway Pressure on Cheyne-Stokes Respiration During Sleep in Congestive Heart Failure," *Chest*, vol. 116, pp. 1550-1557, Dec. 1999.

LaFond, C. et al "Impact of CPAP on Asthmatic Patients with Obstructive Sleep Apnoea," *Eur Respir J*, vol. 29, pp. 307-311, 2007.

Lanfranchi, P.A. et al, "Prognostic Value of Nocturnal Cheyne-Stokes Respiration in Chronic Heart Failure," *Circulation*, pp. 1435-1440, 1999.

Leung, R. et al, "Sleep Apnea and Cardiovascular Disease," *Am J Respir Crit Care Med*, vol. 164, pp. 2147-2165, 2001.

Liem, L.B., "EP 101: Ventricular Tachycardia", EP Lab Digest, v. 7, No. 8, Aug. 2007.

Malkin R. et al., "The Effect of Inducing Ventricular Fibrillation with 50-Hz Pacing Versus T are Stimulation on the Ability to Defibrillate", Pacing And Clinical Electrophysiology, vol. 21, issue 5, May 1998.

Mathew, O., "Effects of Transient Intrathoracic Pressure Changes (hiccups) on Systemic Arterial Pressure," *J Appl Physiol*, vol. 83, pp. 371-375, 1997.

Mitsuyana, T. et al, "Diaphragm Pacing With the Spinal Cord Stimulator," *Aeta Neurochir*, 87:89-92, 2003.

Norton, J., "Toward Consistent Definitions for Preload and Afterload," *Advan in Physiol Edu*, vol. 25, pp. 53-61, Mar. 2001.

Noshiro, M. et al., "Method of Electrophrenic Respiration for Producing a Natural Respiratory Flow Rate Using Feedback Control of Tidal Volume Waveform," *Med. & Bio. Eng. & Comput.*, 20:765-71, Nov. 1982.

Patroniti, M.D., et al "Sigh Improves Gas Exchange and Lung Volume in Patients with Acute Respiratory Distress Syndrome Undergoing Pressure Support Ventilation," *Anesthesiology*, 96:788-794, 2002.

Peters, J. et al, "Negative Intrathoracic Pressue Decreases Independently Left Ventricular Filling and Emptying," *American Physiological Society*, pp. H120-H131, 1989.

Pinsky, M. "Cardiovascular Issues in Respiratory Care," *Chest*, vol. 128, pp. 592-597, Nov. 2005.

"Quadripolar Pacing Addresses Issues Without Moving Leads," *Diagnostic & Invasive Cardiology*, 1 page, Jun. 1, 2010, Scranton Gillette Communications.

Reeve, C., "New Implantable Breathing Device," University Hospitals of Cleveland, pp. 1-4, 2003.

Reeve, C., Christopher Reeve Paralysis Foundation Questions & Answers, pp. 1-3, Mar. 13, 2003.

Sauermann, S. et al, "Computer Aided Adjustment of the Phrenic Pacemaker; Automatic Functions. Documentation, and Quality Control," *Artificial Organs*, 21(3):216-217, 1997.

Schmit, B. D. et al, "Laparoscopic Placement of Electrodes for Diaphragm Pacing Using Stimulation to Locate the Phrenic Nerve Motor Points," *Transactions on Rehabilitation Engineering*, 6(4):382-390, Dec. 1998.

Schultz, R. et al "Nocturnal Periodic Breathing in Primary Pulmonary Hypertension," *Eur Respir J*, vol. 19, pp. 658-663, 2002.

Series, F. et al, "Assessment of Upper Airway Stabilizing Forces with the Use of Phrenic Nerve Stimulation in Conscious Humans," *J Appl Physiol*, vol. 94, pp. 2289-2295, 2003.

Series, F. et al, "Increasing the Functional Residual Capacity May Reverse Obstructive Sleep Apnea Sleep," 11(4):349-353, 1988.

Shaul, D.B. et al, "Thoracoscopic Placement of Phrenic Nerve Electrodes for Diaphragmatic Pacing in Children," *Journal of Pediatric Surgery*, 37:974-978, Jul. 2002.

Shier, D. et al, *Hole's Human Anatomy & Physiology*, pp. 798 (2 pages total), Jan. 6, 2009.

Simon, P. et al, "Vagal Feedback in the Entrainment of Respiration to Mechanical Ventilation in Sleeping Humans," *J. App. Physiol*, 89:760-769, 2000.

Sin, D. "Effects of Continuous Positive Airway Pressure on Cardiovascular Outcomes in Heart Failure Patients With and Without Cheyne-Stokes Respiration," *Circulation*, 102:61-66, Jul. 4, 2000.

Sorli, J. et al., "Ventilatory Assist Using Electrical Stimulation of AJdominal Muscles," *IEEE Transactions of Rehabilitation Engineering*, vol. 4, No. 1, pp. 1-6, Mar. 1996.

Taira, T. et al, "Phrenic Nerve Stimulation for Diaphragm Pacing With a Spinal Cord Stimulator," *Surg Neurol.* 59:128-132, 2003.

Van Houwelingen, K. et al "The Sleep Apnoea Syndromes," *European Heart Journal*, vol. 20, pp. 858-866, Jun. 1999.

Wolk, R. et al "Sleep-Disordered Breathing and Cardiovascular Disease," *Circulation*, vol. 108, pp. 9-12, Jul. 2003.

Yim, S. et al "Continuous Positive Airway Pressure for Asthma: Not a Big Stretch?," *Eur Respir J*, vol. 29, pp. 226-228, 2007.

* cited by examiner

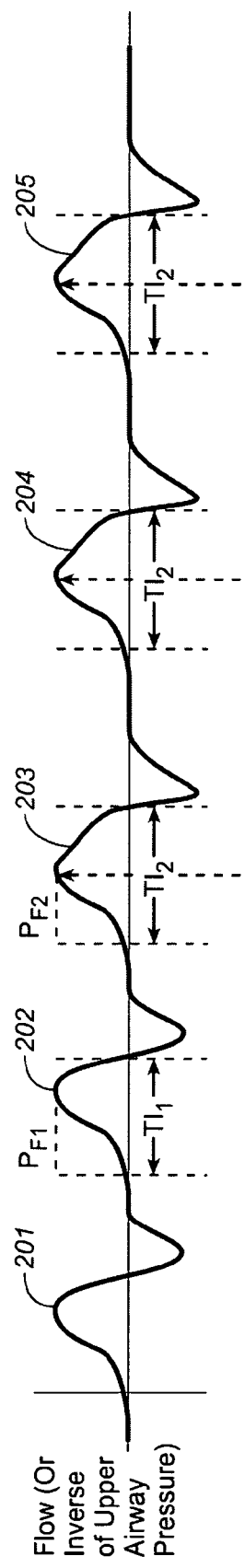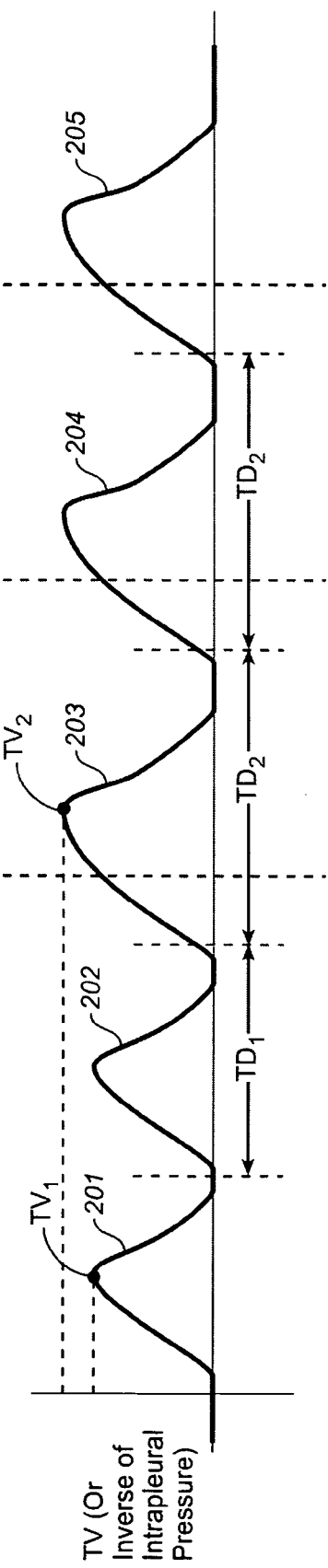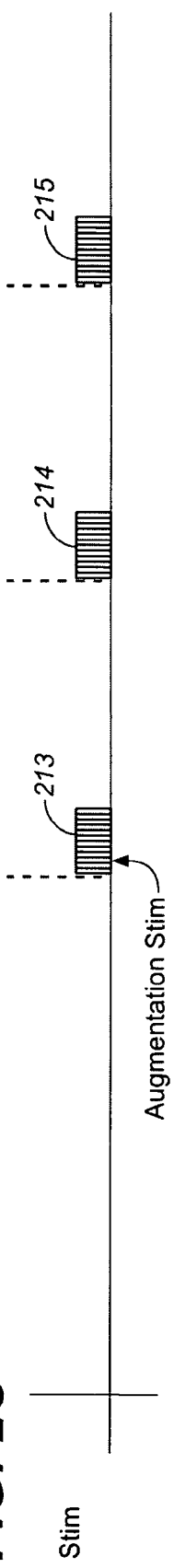

EMG Diaphragm (Intrinsic Activity)

Flow

TV

Stimulation Marker

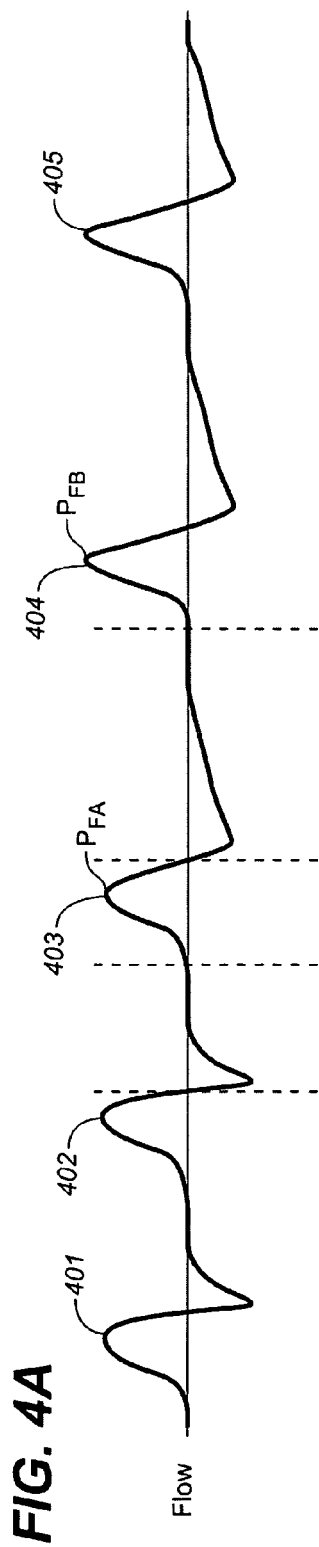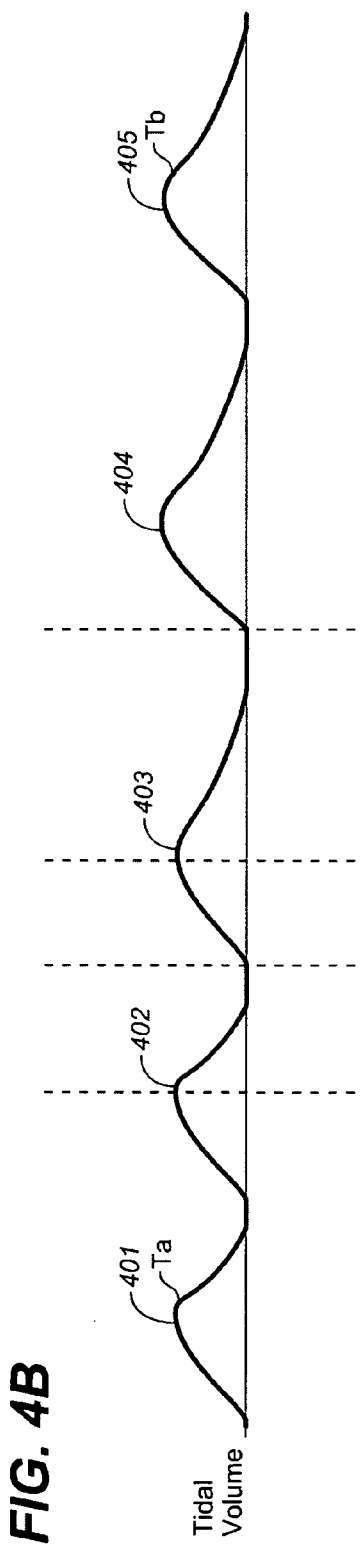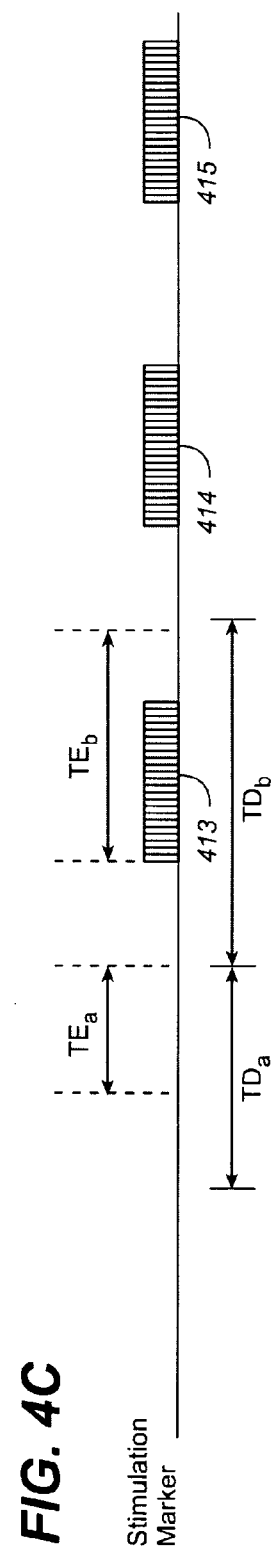

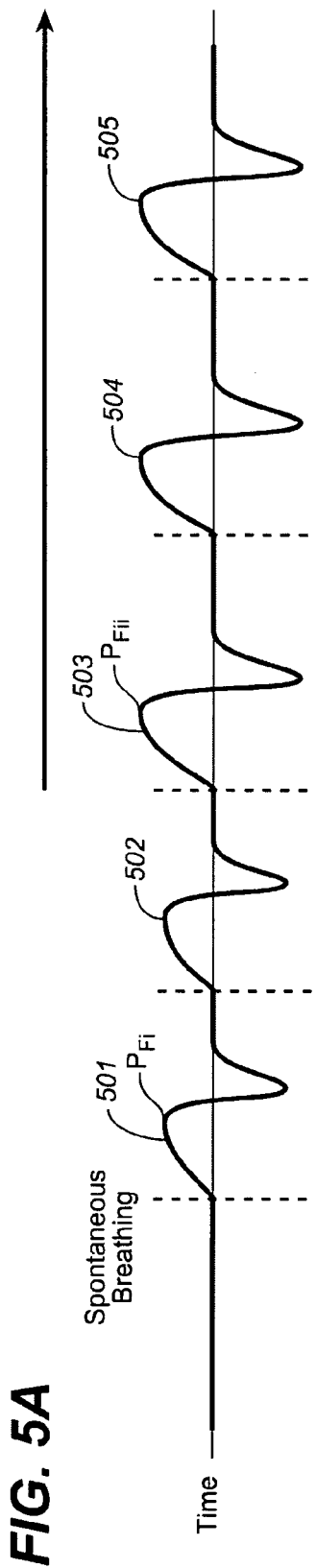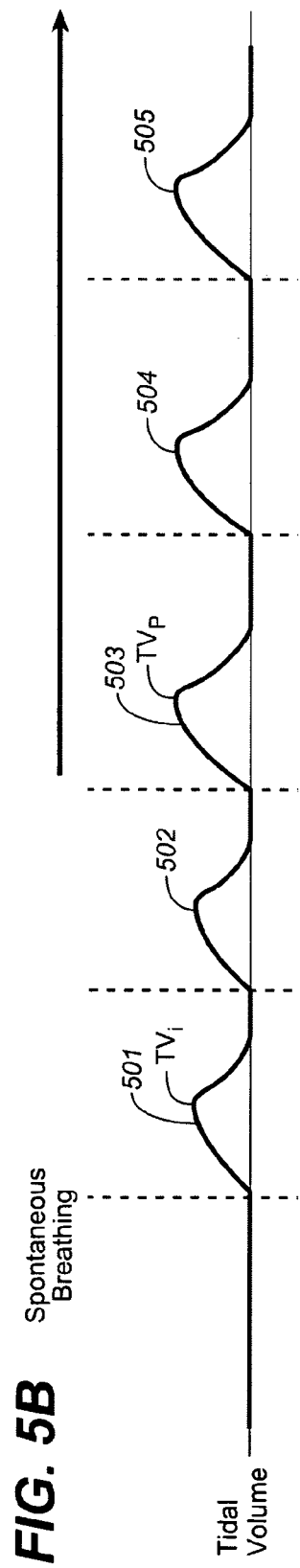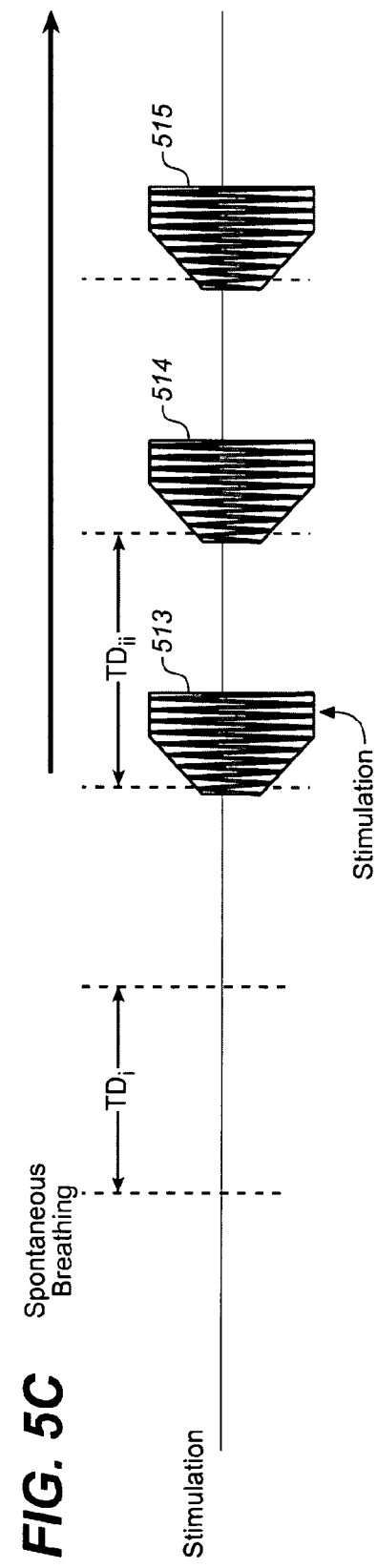

DEVICE AND METHOD FOR TREATING DISORDERS OF THE CARDIOVASCULAR SYSTEM OR HEART

RELATED APPLICATION DATA

This application claims priority of U.S. Application Ser. No. 60/925/024 and is a continuation in part U.S. application Ser. No. 12/069,823 filed Feb. 13, 2008, and of U.S. application Ser. No. 12/044,932 filed Dec. 21, 2007; and of U.S. application Ser. No. 11/981,342 filed Oct. 31, 2007; and of U.S. application Ser. No. 11/480,074 filed Jun. 29, 2006; and of U.S. application Ser. No. 11/271,315 filed Nov. 10, 2005; and of U.S. application Ser. No. 11/271,554 filed Nov. 10, 2005; and of U.S. application Ser. No. 11/271,353 filed Nov. 10, 2005; and of U.S. application Ser. No. 11/271,264 filed Nov. 10, 2005; and of U.S. patent application Ser. No. 10/966,487 filed Oct. 15, 2004; and of U.S. application Ser. No. 11/480,074 filed Jun. 29, 2006 which is a continuation in part of U.S. application Ser. No. 11/271,726 filed Nov. 10, 2005 which is a continuation in part of U.S. application Ser. No. 10/966,484 filed Oct. 15, 2004; U.S. application Ser. No. 10/966,474, filed Oct. 15, 2004; U.S. application Ser. No. 10/966,421, filed Oct. 15, 2004; and U.S. application Ser. No. 10/966,472 filed Oct. 15, 2004 which are continuations in part of U.S. application Ser. No. 10/686,891 filed Oct. 15, 2003 entitled: BREATHING DISORDER DETECTION AND THERAPY DELIVERY DEVICE AND METHOD all of which are incorporated completely and without limitation herein by reference.

FIELD OF THE INVENTION

The present invention relates to treating heart failure (or dysfunction) and other cardiovascular disorders.

BACKGROUND OF THE INVENTION

Heart failure is a complex disease with many forms and causes. In general heart failure is defined as a condition where the cardiac output is not adequate to meet the metabolic needs of the body, either at rest or with exercise. Heart failure may be preceded by heart dysfunction, including, but not limited to ventricular dysfunction.

There are two forms of heart failure, one where the hearts ability to expel the blood is impaired (systolic heart failure), another where there is a defect in ventricular filling (diastolic heart failure). Each can occur in isolation or together.

Current treatments for heart failure are available to slow the progress of the disease but do not cure the disease. Despite all the current therapeutic options, studies show that more then half of heart failure patients die within 5 years of their diagnosis.

Accordingly it would be desirable to provide new and useful treatments for heart failure or other cardiac/cardiovascular disease.

Pacemakers have been useful where there are cardiac bradyarrhythmias. Defibrillators are primarily used to prevent sudden cardiac death and therefore have not improved the status of heart failure patients nor have they improved quality of life. Cardiac Resynchronization Therapy devices (CRTs) have been useful or in patients with significant interventricular delay or in preventing cardiac tachyarrhythmias or sudden cardiac death (CRT-Ds). There are many heart failure patients who may not substantially benefit from one or more of these treatments or may not have an improved quality of life from such treatments. For example, CRTs have not been approved for patients with ejections fractions greater than 35% and thus are not available for diastolic heart failure patients who typically have ejection fractions greater than 50%, or for systolic patients with an ejection fraction greater than 35%. Some studies show diastolic heart failure to account for up to ⅓ of the patients presenting with heart failure. In addition, because the current treatments do not cure heart failure, additional treatment that may be used in combination with existing treatment may be beneficial to the patients.

Many of the drugs such as calcium channel blockers, beta blockers, ACE inhibitors, diuretics, nitrates have had varying degrees of effect on different manifestations of heart failure. However, not all are useful to treat all heart failure patients. Furthermore, due to side effects some patients withdraw from treatment. Pharmacological therapeutic approaches to diastolic heart failure currently recommend diuretics and nitrates while the efficacy is uncertain for all diastolic heart failure patients with calcium channel blockers, beta blockers, ACE inhibitors. Inotropic agents are not recommended for diastolic patients. Accordingly it would be desirable to provide treatment for heart failure that may be used alone or in combination with other heart failure treatments. It would also be desirable to provide alternative or supplementary treatment for diastolic heart failure patients.

Another cardiovascular condition that may exist with or without heart failure is hypertension. Hypertension is believed to worsen heart failure. It is also believed that hypertension may lead to diastolic heart failure. Studies have shown that treatment of hypertension reduces the incidence of heart failure by 30% to 50%. Accordingly it would be desirable to provide a treatment for hypertension.

In addition, a large percentage of heart failure patients also suffer from one or more forms of sleep apnea: obstructive sleep apnea or central sleep apnea, (each of which have significant clinical differences), or mixed apneas. These conditions are believed to worsen progression of heart failure. Obstructive sleep apnea is also believed to contribute to the development of heart failure, particularly through hypertension.

Oxygen desaturations at night, changes in intrathoracic pressure, and arousals may adversely effect cardiac function and eventually result in an imbalance between myocardial oxygen delivery and consumption. In heart failure patients with sleep apnea, there is believed to be an increased incidence of atrial fibrillation, ventricular arrhythmias and low left ventricular ejection fraction. Atrial fibrillation may be caused in part by increased right heart afterload due to hypoxic vasoconstriction which produces pulmonary hypertension. Periodic breathing such as Cheyne-Stokes associated with CSA, create wide fluctuations in intrathoracic pressure with a negative cardiovascular impact. Central sleep apnea sometimes goes undiagnosed in heart failure patients. The untreated central sleep apnea may trigger a negative chain of events that leads to worsening of heart failure.

Obstructive sleep apnea is believed to elicit a series of mechanical, hemodynamic, chemical, neural and inflammatory responses with adverse consequences for the cardiovascular system for example, as described in *Sleep Apnea and Heart Failure Part I: Obstructive Sleep Apnea*. Bradley, Douglas T, MD, Floras, John S., MD D Phil, Circulation Apr. 1, 2003. Many of these effects are believed to exacerbate conditions of heart failure. Among these responses, increases in blood pressure as well as increases in sympathetic activity are associated with obstructive apneas.

Accordingly it would be desirable to treat sleep apnea in heart failure to reduce the negative effects of the apnea on the patient's disease status.

CPAP is the most common treatment for obstructive sleep apnea and has been proposed for central sleep apnea. CPAP requires an external device and patient compliance. In addition, its cardiovascular effects are currently unclear and some researchers believe that it can exacerbate heart failure in some patients, particularly where positive forced pressure has a negative effect on a heart failure patient, such as, for example, in patients where a reduced ventricular filling would significantly reduce cardiac output. Diaphragm stimulation has been proposed to treat central sleep apnea by stimulating when apnea has occurred. However, the stimulation is provided after the apnea event has occurred rather than preventing the apnea event. Hypoglossal nerve stimulation has been proposed to treat obstructive sleep apnea by increasing patency in the upper airway to enable respiration. But it is believed would not provide additional benefit to heart failure patients other than that of treating the obstructive apnea.

It would accordingly be desirable to provide a treatment for sleep apnea that has a symbiotic therapeutic effect in treating heart failure or other cardiac/cardiovascular disease.

It would further be desirable to provide a treatment for heart failure patients with sleep apnea that provides a separate or additional function of treating heart failure.

Research has shown that voluntary control of breathing can improve cardiac disease, including hypertension and heart failure. It is believed that the reason for this is a biofeedback that exists between the cardiac and respiratory systems due to baroreceptor based reflexes, and also a common central nervous control. Biofeedback systems for breathing control have been provided. However, they require patient compliance and diligence. Furthermore, because they require patient compliance, the therapy can only occur during waking hours.

SUMMARY OF THE INVENTION

In accordance with the invention, stimulation is provided to the diaphragm or phrenic nerve to elicit a diaphragm response to thereby provide a therapeutic effect for a heart failure or other cardiac or cardiovascular patient.

In accordance with one aspect of the invention, stimulation to elicit a diaphragm response is provided to increase or normalize lung volume and in particular to increase functional residual capacity. It is believed that stimulation to increase or to normalize lung volume or functional residual capacity may have one or more effects that may be therapeutic to cardiovascular or heart failure patients. Normalizing herein may include for example, bringing a physiological parameter into a normal or healthy region for patients or for a particular patient, or to a level appropriate for a condition or state of a patient.

In accordance with another aspect of the invention stimulation is provided to control breathing to reduce respiration rate and thereby reduce hypertension, reduce sympathetic nerve bias, and/or provide improved blood gas levels.

In accordance with another aspect of the invention stimulation is provided to control minute ventilation to therapeutically effect blood gas levels.

In accordance with another aspect of the invention, stimulation is provided to create a deep inspiration or an increased tidal volume to thereby reduce sympathetic nerve bias, improve blood gas levels, stimulate reflexes for example the Hering-Bruer reflex related to activating stretch receptors, increase lung volume, normalize or reset breathing or provide other beneficial therapies to improve cardiovascular function or heart failure condition.

In accordance with another aspect of the invention stimulation may be provided to manipulate intrathoracic pressure to thereby produce a therapeutic effect. According to one embodiment, stimulation is provided to reduce intrathoracic pressure to thereby reduce preload on the heart.

In accordance with another aspect of the invention stimulation is provided to reduce breathing disorders to thereby improve condition of a heart failure patient.

In accordance with another aspect of the invention a combined cardiac rhythm management device and diaphragm/phrenic nerve stimulation device is provided to provide an enhanced combined treatment device.

These and other aspects of the invention are set forth herein in the abstract, specification and claims.

DESCRIPTION OF THE DRAWINGS

FIGS. 2A, 2B and 2C illustrate respectively, flow, tidal volume and stimulation envelope signals corresponding to use of a device and method in accordance with an aspect of the invention.

FIGS. 4A, 4B, and 4C illustrate respectively, flow, tidal volume and stimulation envelope signals corresponding to use of a device and method in accordance with an aspect of the invention.

FIGS. 5A, 5B, and 5C illustrate respectively, flow, tidal volume and stimulation envelope signals corresponding to use of a device and method in accordance with an aspect of the invention.

DETAILED DESCRIPTION

In accordance with one aspect of the invention, stimulation to elicit a diaphragm response is provided to increase or normalize lung volume and in particular to increase functional residual capacity. It is believed that stimulation to increase or to normalize lung volume or functional residual capacity may have one or more effects that may be therapeutic to cardiovascular or heart failure patients.

In accordance with this aspect of the invention stimulation may be provided using a device or method as described in one or more of the related patent applications set forth herein, to increase or normalize lung volume or functional residual capacity. For example, a bias stimulation may be provided to increase functional residual capacity or to bias lung volume for a period of time. It is believed that increasing functional residual capacity may have one or more therapeutic effects for heart failure or other cardiovascular patients, such as, for example, reducing effort required to breathe; improving gas exchange, improving $SaO_2$ levels; providing a buffer to reduce fluctuations in blood gas levels and to reduce the likelihood of crossing the $PCO_2$ apneic threshold; and reducing episodes of obstructive apnea in OSA patients and central sleep apnea episodes. Such buffer may also stabilize blood gases to counter fluctuations in gas levels caused by circulatory delay that may lead to Cheyne-Stokes respiration and Central Sleep Apnea. Other stimulation may be provided to achieve improved $SaO_2$ levels or gas levels, for example, as set forth in the related patent applications which are incorporated completely and without limitation herein by reference.

Other stimulation may be provided that may have the effect of normalizing lung volume, including but not limited to low frequency stimulation, low energy stimulation, or deep inspiration stimulation. These various stimulation techniques may also be provided or configured to have the effect of increasing $SaO_2$ levels to reduce load on the heart.

Figure 1A:
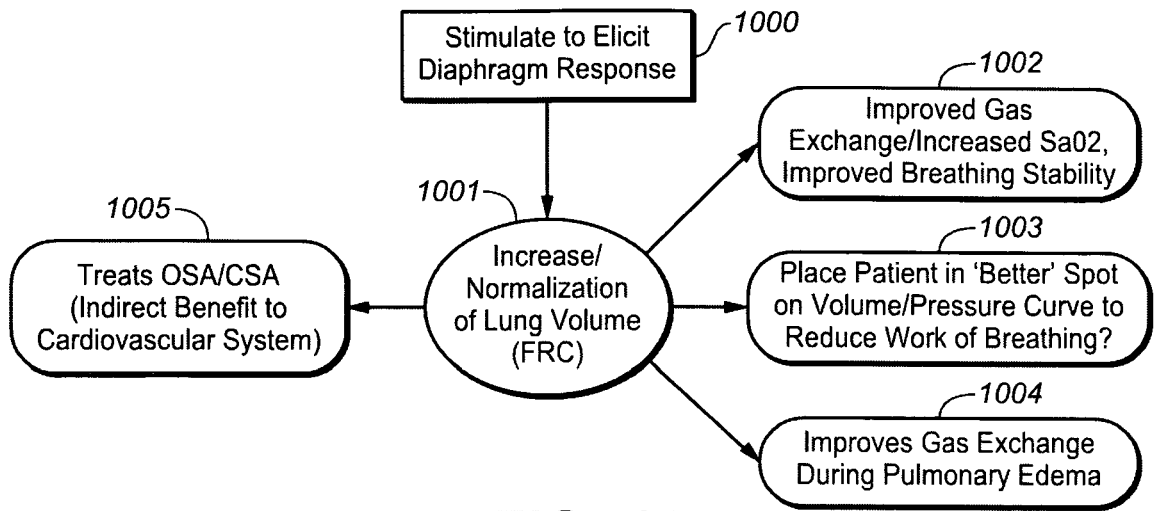
FIG. 1A is a chart illustrating examples of possible beneficial effects of stimulation in accordance with an aspect of the invention.

FIG. 1A illustrates stimulation provided with a device or method in accordance with the invention. Stimulation is provided using a device or method for stimulating tissue to elicit a diaphragm response 1000. Stimulation increases or normalizes lung volume or FRC 1001. The increase or normalization or lung volume may improve gas exchange; increase SaO2, and/or improve breathing stability 1002. The increase or normalization of lung volume or FRC may move a patient to a more optimal location on the volume pressure curve 1003 as described in more detail with respect to FIG. 1B. Providing stimulation to increase FRC may also allow improved gas exchange during pulmonary edema where lung inflation creates a gradient for liquid movement from alveolar space to the extra-interstitium 1004. It is believed that moving fluids to the interstitial space will improve ventilation because removal of fluids from the alveolar region will permit improved gas exchange. An increase or normalization of lung volume or FRC may also treat OSA or CSA in patients with OSA (obstructive sleep apnea) or CSA (central sleep apnea) and thereby benefit the cardiovascular system 1005. For example, one or more devices and methods described in copending patent applications set forth above may be used to treat OSA or CSA.

Figure 1B:
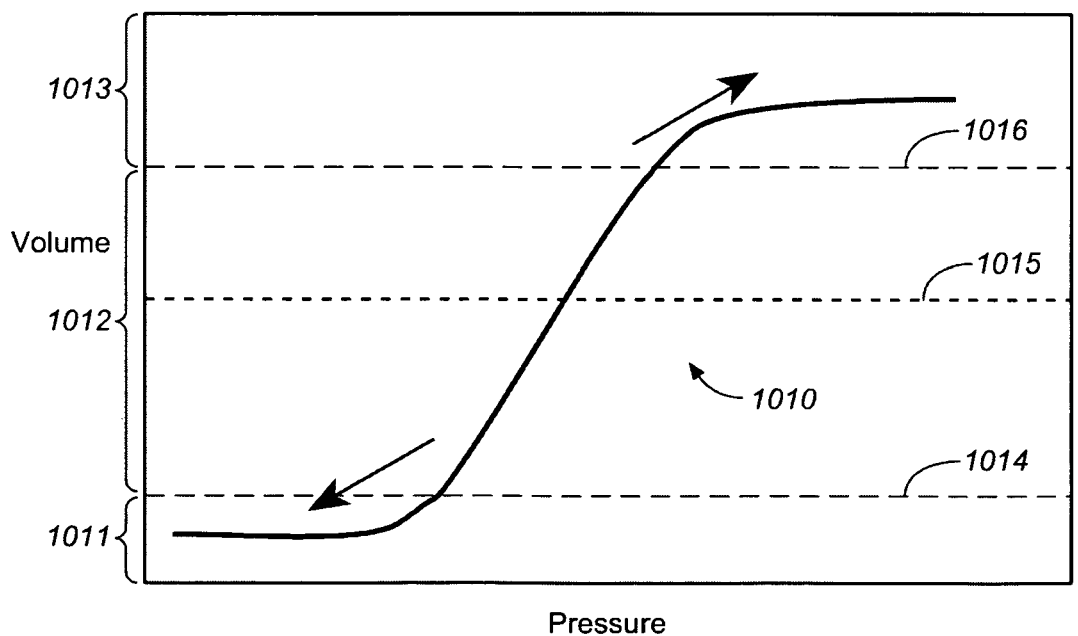
FIG. 1B is a pressure volume curve illustrating use of stimulation in accordance with an aspect of the invention.

FIG. 1B illustrates a pressure/volume curve 1010 illustrating a relationship between transthoracic pressure and lung volume. This example illustrates, among other things how stimulation may be provided to reduce breathing effort and/or intrathoracic pressure change for a given inspiration volume. At lower lung volumes 1011, a greater change in pressure is required to increase lung volume a given amount through inspiration, thus providing a greater work of breathing and thereby increasing metabolic requirements and load on heart as well. Similarly at higher lung volumes 1013, greater change in pressure and effort are required to increase lung volume through inspiration. However, in between the lower volumes 1011 and higher volumes 1013 there is a steeper portion of the curve 1012 where at a given lung volume, inspiration produces an efficient increase in lung volume with less change in pressure required to effect a given volume and therefore less effort required by the respiratory muscles to produce a given change in pressure. It is believed that an increase in required effort to breathe may result in poorer breathing or less effort and gas exchange, particularly in heart failure patients. It is also believed that greater fluctuations in intrathoracic pressure may contribute the conditions affecting heart failure. Thus in accordance with one aspect of the invention, stimulation may be provided to increase resting lung volume so that greater breathing efficiency and gas exchange is provided. Where a patient's normal resting lung volume or functional residual capacity is typically low, it may be increased. Where a patient's resting lung volume is lower than normal for a healthy individual, it may be normalized so that it is brought to a level where efficient breathing occurs. For example a low lung volume 1014 may be increased to higher lung volumes 1015 or 1016 which are at an efficient volume 1012 on the pressure volume curve 1010.

Stimulation may be provided on a sustained or intermittent basis. Stimulation may be provided when a patient is asleep or awake. In accordance with one aspect of the invention, stimulation is provided to compensate for lung volume lost at the onset of sleep or during sleep. In accordance with one aspect of the invention the stimulator may be turned on by the patient prior to sleeping or may be triggered by a sensed parameter or real time clock. A sensor may be used to sense one or more physiological parameters indicating onset or a specific stage of sleep. Other sensors may sense one or more conditions that may be used to determine appropriate times or parameters for stimulation.

In accordance with another aspect of the invention stimulation is provided to control breathing to reduce respiration rate and thereby improve, prevent or slow cardiac disease by reducing hypertension, reducing sympathetic nerve activation, providing SaO2 levels, and/or increasing cardiac output. It is believed that lowering breathing rate will provide a decrease in cardiac rate, and an enhanced vagal response.

In accordance with one aspect of the invention, breathing rate may be controlled by augmenting breathing or stimulating during intrinsic breathing to increase peak tidal volume and/or to increase inspiration duration. Increasing the duration of inspiration or tidal volume it is believed will cause the timing of the next intrinsic breath to be delayed due to the central nervous controller tendency to maintain minute ventilation in absence of any change at the chemoreceptor level. The rate may be continuously slowed by detecting each intrinsic breath and providing stimulation or augmenting until the duration of inspiration, tidal volume or exhalation rate is at a level that brings the breathing rate to a desired rate which is reduced by the central nervous control of minute ventilation.

FIGS. 2A to 2C illustrate stimulation during intrinsic breathing in accordance with one aspect of the invention. FIG. 2A illustrates flow for breaths 201, 202, 203, 204 and 205. FIG. 2B illustrates tidal volume of breaths 201, 202, 203, 204, and 205. Breaths 201, 202 are intrinsic breaths. Breaths 203, 204, and 205 are intrinsic breaths that are augmented by stimulation configured to elicit a diaphragm response as illustrated schematically by stimulation markers 213, 214, and 215.

Stimulation is initiated at a period of time during inspiration and is provided for a period a time in a manner configured to increase tidal volume. Stimulation during intrinsic breathing and augmenting breathing are described in one or more related applications as set forth herein which are incorporated completely and without limitation herein by reference. The tidal volume $TV_2$ of the breaths 203, 204, 205 where inspiration is augmented is greater than the tidal volume $TV_1$ of the intrinsic breaths 201, 202. According to one variation, the peak flow during stimulation $Pf_2$ may be configured as shown to be close to the peak flow $Pf_1$ during intrinsic breathing. The inspiration duration $TI_1$ of intrinsic breathing is shorter than the inspiration duration $TI_2$ of augmented breaths 203, 204, 205. The duration $TD_1$ of intrinsic breathing is increased to duration $TD_2$ and with stimulation signals 213 214, 215, to achieve a desired rate.

In accordance with another aspect of the invention, stimulation during intrinsic breathing may be provided to inhibit onset of inspiration. According to an aspect, stimulation may be provided during exhalation to inhibit onset of an inspiration thereby slowing breathing rate. According to an aspect, stimulation may be provided to extend exhalation thereby delaying the onset of a subsequent inspiration. According to an aspect, stimulation may be provided at a low energy, low level or low frequency to inhibit onset of an inspiration, thereby slowing breathing rate. Examples of low energy, low level and/or low frequency stimulation are set forth in the related applications herein.

The rate of intrinsic breathing may be controlled by delaying intrinsic breaths with low energy (for example a lower amplitude, frequency and/or pulse width than desired for paced breathing) diaphragm stimulation provided during intrinsic breathing.

According to one aspect, low energy stimulation may be provided during intrinsic breathing, delaying onset of the next breath and thereby slowing breathing rate. According to another aspect, stimulation may be initiated sufficiently prior to the onset of the next breath so as to reduce the likelihood that the stimulation would trigger a breath. A combination of lower energy stimulation and timing the stimulation sufficiently prior to the onset of the next breath may be used to slow breathing rate.

Figure 3A:
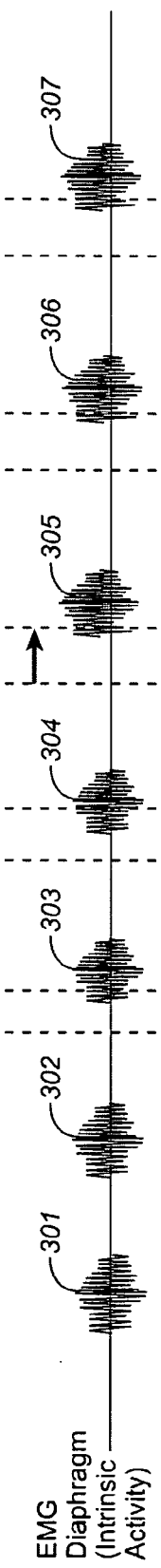
FIGS. 3A, 3B, 3C and 3D illustrate respectively, EMG, flow, tidal volume and stimulation envelope signals corresponding to use of a device and method in accordance with an aspect of the invention.
Figure 3B:
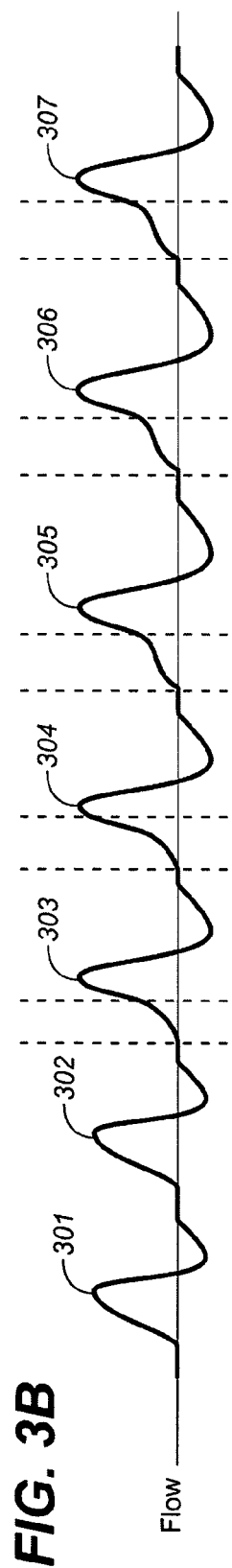
Figure 3C:
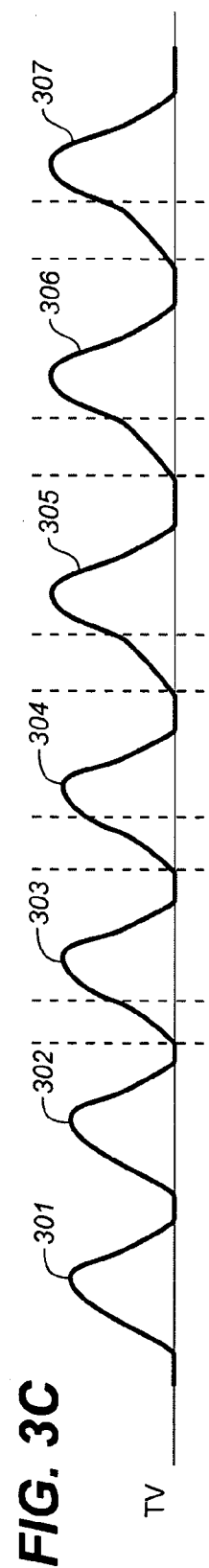
Figure 3D:
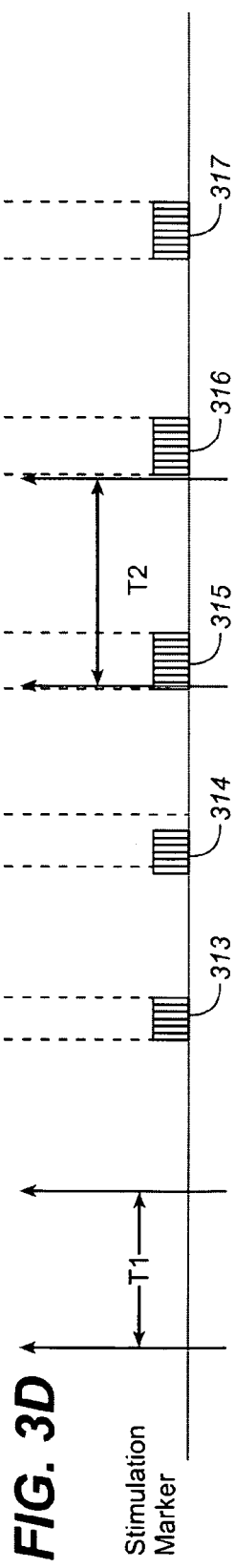

FIGS. 3A to 3D illustrate stimulation provided to slow breathing in accordance with one aspect of the invention. FIG. 3A illustrates intrinsic diaphragm EMG activity corresponding to breaths 301 through 307. FIGS. 3B and 3C respectively illustrate flow and tidal volume corresponding to breaths 301 through 307. FIG. 3D illustrates stimulation envelopes corresponding to stimulation signals 313, 314, 315, 316, and 317 provided prior to onset of breaths 303, 304, 305, 306, and 307 respectively. Stimulation 313, 314, 315, 316, 317 is provided prior to the onset of breath 303, 304, 305, 306, 307 respectively, as determined, for example, by a model that predicts the onset of breathing or by the actual detection of the intrinsic diaphragm EMG activity (FIG. 3A). Stimulation is sustained for a period of time. For example, the stimulation may be provided until the onset of the intrinsic breath is detected by the EMG signal. As illustrated, the stimulation increases the duration of a respiration cycle T2 with respect to the duration Ti of an intrinsic breathing cycle. As further illustrated, intrinsic breathing cycles 303 to 307 may have greater flow or tidal volume to compensate for the slower breathing rate that is induced by the stimulation.

In accordance with another aspect of the invention, stimulation to increase tidal volume or inspiration duration may be provided in combination with stimulation during exhalation to inhibit the onset of the next inspiration.

In accordance with another aspect of the invention stimulation may be provided to delay exhalation by stimulating at the end of inspiration at a level that slows exhalation. Such stimulation may be provided by stimulating during intrinsic breathing or by providing paced breathing for example that maintains minute ventilation while providing a slower rate of breathing.

FIGS. 4A-4C illustrate stimulation during intrinsic breathing in accordance with one aspect of the invention. FIG. 4A illustrates flow for breaths 401, 402, 403, 404 and 405. FIG. 4B illustrates tidal volume of breaths 401, 402, 403, 404 and 405. Breaths 401, 402 are intrinsic breaths. Breaths 403, 404, and 405 are intrinsic breaths that are augmented by stimulation configured to elicit a diaphragm response as illustrated schematically by stimulation markers 413, 414, and 415. Stimulation is initiated at a period of time at the end of inspiration and is provided for a period a time through the exhalation period. Detection and stimulation techniques are set forth, for example in related applications hereto. Stimulation may be provided at a low energy level including at a low frequency. Stimulation during intrinsic breathing and augmenting breathing, low level and/or low frequency are described in one or more related applications as set forth herein which are incorporated completely and without limitation herein by reference. The peak flow during stimulation $Pf_b$ may be greater than the peak flow $Pf_a$ during intrinsic breaths 401, 402 as illustrated. The peak flow during stimulation $Pf_b$ may be also not be greater than the peak flow $Pf_a$ during intrinsic breaths 401, 402. Similarly tidal volume Tb is for breaths 404, 405 after stimulation 413 and 414 respectively. Such greater flow or tidal volume may intrinsically compensate for the slower breathing rate that is induced by the stimulation. It is believed that stimulation during exhalation inhibits onset of inspiration. The stimulation also slows exhalation (i.e., during the period which exhalation is occurring at a relatively faster rate) so that the exhalation duration $TE_b$ during stimulation is greater than the intrinsic exhalation duration $TE_a$. Exhalation is slowed by stimulation thus slowing the overall rate of breathing. The duration of the intrinsic breathing respiration cycle $TD_a$ is increased to duration $TD_b$ during stimulation, thus reducing the breathing rate to a desired rate.

Stimulation may also be provided to slow or control breathing rate in a manner that provides a paced breath with controlled exhalation as illustrated for example in U.S. patent application Ser. No. 10/966,474, filed Oct. 15, 2004 and U.S. patent application Ser. No. 10/966,472, filed on Oct. 15, 2004.

FIGS. 5A to 5C illustrate stimulation used to control breathing and breathing rate in accordance with the invention. Breaths 501 and 502 are intrinsic breaths occurring at a rate such that the duration of the respiration cycle is TDi and having tidal volume TVi and peak flow PFi. Breaths 503, 504 and 505 are paced breaths with higher tidal volume TVp and peak flow PFp. Peak flow PFp may be controlled to be at a level substantially the same as, higher, or lower than intrinsic peak flow. Paced breathing is provided in a manner in which breathing is controlled or taken over by stimulated breathing. Examples of techniques for controlling breathing, respiratory drive and/or taking over breathing are set forth in related applications incorporated completely and without limitation herein by reference. In general greater tidal volume permits a reduction in breathing rate or an increase in duration of breathing cycle to TDii while maintaining minute ventilation. FIG. 5C illustrates stimulation envelopes 513, 514, 515 respectively corresponding to stimulated breaths 503, 504, 505.

In accordance with another aspect of the invention stimulation is provided to control minute ventilation to therapeutically affect blood gas levels. Examples of controlling minute ventilation are set forth for example in U.S. patent application Ser. No. 10/966,474. Such stimulation may be provided, for example, during sleep to thereby increase or normalize $SaO_2$ levels during sleep. In accordance with one aspect of the invention minute ventilation is controlled to normalize $SaO_2$ levels while not decreasing $PaCO_2$ levels close to the apneic threshold. According to this aspect minute ventilation may be actively controlled using sensors to sense $SaO_2$ or $PaCO_2$ levels. Weaning off of pacing may be desirable to insure that the intrinsic drive to breath is still present. Paced breathing may be calibrated, for example at implant or adjusted during device use, so that the device is able to provide the appropriate minute ventilation at each pacing setting. This information may be obtained for example through sleep studies where the device is designed to provide stimulation during sleep.

In accordance with another aspect of the invention, stimulation is provided to create a deep inspiration or an increased tidal volume to thereby reduce sympathetic nerve bias, improve blood gas levels, stimulate reflexes (for example the Hering-Bruer reflex related to activating stretch receptors), increase lung volume, normalize or reset breathing (one or more parameters) or provide other beneficial therapies to improve cardiovascular function or heart failure condition.

Examples of creating deep inspiration are set forth in U.S. patent application Ser. No. 11/272,353 filed Nov. 10, 2005. While these examples refer to using deep inspiration to treat apnea, similar techniques for stimulation may be used to create deep inspiration breaths for improving cardiovascular function or treating heart failure. Stimulation may be provided during intrinsic inspiration or in between inspiration cycles.

In accordance with another aspect of the invention stimulation may be provided to manipulate intrathoracic pressure to thereby produce a therapeutic effect.

According to one embodiment, stimulation is provided to reduce intrathoracic pressure through induced contraction of the right and/or left hemidiaphragm. It is believed that for some patients, reduction in intrathoracic pressure may have a beneficial effect on the patient's cardiovascular function or condition. For example, a reduced intrathoracic pressure may increase cardiac output at least in part through an increase in ventricular filling; and reduce pulmonary arterial pressure in relation to atmospheric pressure which would reduce right ventricular afterload. A reduced intrathoracic pressure may also provide a decrease in filling pressure in the right ventricle and may also thereby improve systemic venous return. A reduced intrathoracic pressure may also provide better coronary artery perfusion.

In accordance with one aspect of the invention, patients with heart failure manifesting in poor ventricular filling may be treated with stimulation to reduce intrathoracic pressure. In accordance with one aspect of the invention, patients with diastolic heart failure may be treated with stimulation to reduce intrathoracic pressure. In accordance with another aspect of the invention stimulation to reduce intrathoracic pressure may be provided to patients who are hypovolemic where the therapeutic effects of improved ventricular filling and venous return would be particularly beneficial.

According one aspect of the invention stimulation is provided to elicit a diaphragm response to cause a reduced intrathoracic pressure. The stimulation is provided at a level that does not elicit a breath, in other words, where intrinsic breathing continues to occur. Examples of stimulation such as bias stimulation and low energy or low frequency stimulation are described in related applications set forth herein. The stimulation eliciting a reduced intrathoracic pressure may be sustained or intermittent. Stimulation is preferably provided when a patient is sleeping but may also be provided when a patient is awake.

In accordance with one aspect of the invention, stimulation may be provided to one hemidiaphragm to elicit a change in intrathoracic pressure in the respective side of the thoracic cavity. For example the right hemidiaphragm may be stimulated to cause a reduced intrathoracic pressure primarily in the right thoracic cavity to thereby effect the right side of the hear to a greater degree than the left. Or stimulating unilaterally on the diaphragm may serve to minimize the pressure changes that the heart is exposed to. This may be beneficial when an increased lung volume is desired to treat OSA or CSA. Sensors may be used to sense arterial and venous blood volume so that stimulation may be adjusted based on patient's blood volume state. For example, stimulation may be increased or turned on when the patient is in a hypo volemic state where in a particular patient a greater benefit would be produced with a more negative intrathoracic pressure. Such sensors may include, for example, impedance (plethysmography) sensors used to monitor fluid levels in the body. Separate electrodes, or existing stimulation electrodes may be used in a configuration or with frequencies that can determine resistance and/or reactance) Fluid volume changes may, for example, be monitored based on a baseline established with the sensors and a hyper or hypo volemic state may be detected.

In accordance with another aspect of the invention, stimulation is provided to elicit a diaphragm response that improves heart failure as described above in combination with treating sleep disorders that contribute to or worsen heart failure. Accordingly, stimulation is provided as described in the related patent applications set forth herein, to elicit a diaphragm response to thereby reduce breathing disorders to thereby improve condition of a heart failure patient. One or more specific methods of reducing sleep disordered breathing events and preventing sleep disordered breathing are described in related applications as set forth herein. In accordance with one aspect of the invention, stimulation is provided prior to a physiological trigger of a central or obstructive sleep apnea event in a manner that reduces the occurrence of such events, thus reducing the effects of apnea events that worsen heart failure.

In accordance with another aspect of the invention a combined cardiac rhythm management device and diaphragm/phrenic nerve stimulation device is provided to provide an enhanced combined treatment device. In accordance with this aspect of the invention, the diaphragm stimulation element may comprise an abdominally placed stimulator positioned on the diaphragm or phrenic nerve, a thoracoscopically placed stimulator positioned on the diaphragm or phrenic nerve, a phrenic nerve stimulator positioned in the neck region on or adjacent the phrenic nerve (transcutaneous, percutaneous, or otherwise implanted); transcutaneous stimulation of the diaphragm through leads at or near the ziphoid region (this may be in combination with a defibrillator function or device that is configured for subcutaneous stimulation of the heart); or a pectorally positioned lead, for example, placed transvenously.

The system may be further enhanced through the ability to avoid negative device/device interactions where a separate controller is used, e.g. for a CRT, pacemaker, ICD or other therapeutic electrical stimulation device. The system may also provide arrhythmia and sleep disorder detection algorithms through sensing of both the cardiac and respiration cycles.

The system may also be included in a combination with a CRM device having a common controller.

The invention claimed is:

1. A method for treating a subject comprising:
    sensing an initial respiration parameter during intrinsic breathing of a subject via at least one electrode positioned internally within the patient;
    synchronizing an electrical stimulation protocol with the sensed respiration parameter via a processor in communication with the at least one electrode; and,
    increasing functional residual lung capacity of the subject by applying the electrical stimulation protocol which comprises a burst or series of pulses to tissue associated with a phrenic nerve or diaphragm tissue to contract a diaphragm at a beginning or during an onset of each intrinsic breathing cycle and sustaining the electrical stimulation protocol such that an intrathoracic pressure is stabilized by increasing a resting lung volume.

2. The method of claim 1 wherein increasing functional residual lung capacity comprises applying the electrical stimulation protocol to the phrenic nerve or diaphragm tissue within a region of the subject selected from the group consisting of an abdomen, a thoracic cavity, a neck region, and a ziphoid region.

3. The method of claim 1 wherein increasing functional residual lung capacity comprises applying the electrical stimulation protocol transvenously to the phrenic nerve or diaphragm tissue.

4. The method of claim 1 further comprising controlling an additional therapeutic electrical stimulation device within the subject independently of or in combination with increasing functional residual lung capacity of the subject.

5. The method of claim 4 wherein controlling an additional therapeutic electrical stimulation device comprises controlling via a second controller.

6. The method of claim 4 wherein the additional electrical stimulation device is selected from the group consisting of a CRT, pacemaker, and ICD.

7. The method of claim 1 wherein increasing functional residual lung capacity comprises sustaining the electrical stimulation protocol such that a respiration rate is reduced.

8. The method of claim 1 wherein the step of increasing functional residual lung capacity comprises electrically stimulating the tissue such that inspiration is augmented.

9. The method of claim 1 wherein the step of increasing functional residual lung capacity comprises pacing each intrinsic breathing cycle such that minute ventilation is maintained or reduced.

10. The method of claim 1 wherein the step of increasing functional residual lung capacity comprises further applying the electrical stimulation protocol during a beginning portion of an inspiration cycle.

11. The method of claim 1 wherein the step of increasing functional residual lung capacity comprises further applying the electrical stimulation protocol at least during an end portion of an inspiration cycle.

12. The method of claim 1 wherein the step of increasing functional residual lung capacity comprises applying the electrical stimulation protocol such that tidal volume is increased during a reduced respiration relative to intrinsic breathing.

13. The method of claim 1 wherein the step of increasing functional residual lung capacity comprises applying the electrical stimulation protocol such that functional residual capacity is increased relative to a non-stimulated breathing.

14. The method of claim 1 wherein the step of increasing functional residual lung capacity comprises improving a gas exchange during pulmonary edema.

15. The method of claim 1 wherein the step of increasing functional residual lung capacity comprises causing a lung inflation gradient such that liquid movement from an alveolar space to an extra-interstitium is improved and pulmonary edema is reduced.

16. The method of claim 1 wherein the step of increasing functional residual lung capacity comprises applying the electrical stimulation protocol such that an exhalation rate is slowed relative to the intrinsic breathing.

17. The method of claim 1 wherein the step of increasing functional residual lung capacity comprises applying the electrical stimulation protocol during the subject's sleep or awake cycle.

18. The method of claim 1 wherein the step of increasing functional residual lung capacity comprises providing a low energy stimulation.

19. The method of claim 1 wherein the step of increasing functional residual lung capacity comprises applying the electrical stimulation protocol such that a resting lung volume is increased relative to the intrinsic breathing.

20. The method of claim 1 wherein the step of increasing functional residual lung capacity comprises applying the electrical stimulation protocol to at least one hemidiaphragm.

21. The method of claim 1 wherein the step of increasing functional residual lung capacity comprises applying the electrical stimulation protocol in a subject having sleep disorder breathing.

22. The method of claim 1 wherein the step of increasing functional residual lung capacity comprises applying the electrical stimulation protocol such that gas exchange in improved.

23. The method of claim 1 wherein the step of increasing functional residual lung capacity comprises applying the electrical stimulation protocol such that hypertension is reduced.

24. The method of claim 1 wherein the intrathoracic pressure is stabilized by increasing the resting lung volume such that a change in the intrathoracic pressure is increased for a given volume through inspiration relative to a non-stimulated breathing cycle.

25. The method of claim 1 wherein the subject comprises a patient having heart failure.

* * * * *